(12) United States Patent
Gerber

(10) Patent No.: US 10,046,175 B2
(45) Date of Patent: Aug. 14, 2018

(54) LIGHT DELIVERY SYSTEMS AND RELATED METHODS OF USE

(71) Applicant: Spectrum Medical Technologies LLC, Vero Beach, FL (US)

(72) Inventor: Mark J. Gerber, Vero Beach, FL (US)

(73) Assignee: Spectrum Medical Technologies, LLC, Vero Beach, FL (US)

( * ) Notice: Subject to any disclaimer, the term of this patent is extended or adjusted under 35 U.S.C. 154(b) by 68 days.

(21) Appl. No.: 14/872,818

(22) Filed: Oct. 1, 2015

(65) Prior Publication Data

US 2016/0082281 A1 Mar. 24, 2016

Related U.S. Application Data

(63) Continuation-in-part of application No. 13/625,357, filed on Sep. 24, 2012, now Pat. No. 9,151,462.
(Continued)

(51) Int. Cl.
*A61N 5/06* (2006.01)
*A61B 19/00* (2006.01)
(Continued)

(52) U.S. Cl.
CPC ........ *A61N 5/0624* (2013.01); *A61B 19/5202* (2013.01); *A61B 90/30* (2016.02);
(Continued)

(58) Field of Classification Search
CPC ....... A61N 5/0624; A61B 90/30; G02B 6/001
(Continued)

(56) References Cited

U.S. PATENT DOCUMENTS 2,259,910 A 10/1941 Rylsky
2,360,663 A 10/1944 Eddy
(Continued)

OTHER PUBLICATIONS

Edmund Optics Inc., 2013, Fiber Optic Ring Light Guides [retrieved on Mar. 18, 2014]. Retrieved from the Internet: <http://www.edmundoptics.com/illumination/fiber-optic-illumination/fib- er-optic-light-guides/fiber-optic-ring-light-guides/1432>.
(Continued)

*Primary Examiner* — Jong-Suk (James) Lee
*Assistant Examiner* — Christopher E Dunay
(74) *Attorney, Agent, or Firm* — McCarter & English, LLP

(57) ABSTRACT

The present disclosure provides for light delivery assemblies and, more particularly to light delivery assemblies/systems that provide light to and/or illuminate/treat predetermined locations (e.g., surgical sites), and related methods of use. An exemplary light delivery assembly (e.g., a surgical site light) includes a shell/housing (e.g., a plastic shell/housing) with a cross-sectional shape similar to an inward-facing asymmetrical C. The shell/housing is shaped to be placed proximal to a site (e.g., surgical site) and emit light onto the site from a plurality of directions while inhibiting the light from radiating away from the outside of the shell/housing. Exemplary light delivery assemblies of the present disclosure can be utilized for a variety of different applications/treatments/uses (e.g., surgical applications, disinfection/sterilization especially UV in the UVC wavelength range, other UV treatment, infrared heating and treatment, therapy, IR light delivery, use of all/other wavelengths of light, etc.).

19 Claims, 13 Drawing Sheets

Related U.S. Application Data

(60) Provisional application No. 62/083,811, filed on Nov. 24, 2014, provisional application No. 61/578,428, filed on Dec. 21, 2011.

(51) Int. Cl.
*F21V 7/00* (2006.01)
*A61B 90/30* (2016.01)
*F21W 131/205* (2006.01)

(52) U.S. Cl.
CPC ......... *A61N 5/0613* (2013.01); *A61N 5/0625* (2013.01); *F21V 7/00* (2013.01); *A61B 2019/5206* (2013.01); *A61N 2005/063* (2013.01); *A61N 2005/0652* (2013.01); *A61N 2005/0659* (2013.01); *A61N 2005/0661* (2013.01); *A61N 2005/0662* (2013.01); *F21W 2131/205* (2013.01)

(58) Field of Classification Search
USPC .... 362/16, 558, 559, 560, 572, 296.01, 307, 362/311.01, 311.06, 347
See application file for complete search history.

(56) References Cited

U.S. PATENT DOCUMENTS

| | | | |
|---|---|---|---|
| 3,474,242 A * | 10/1969 | Forrant | G03B 15/03 362/17 |
| 4,605,990 A | 8/1986 | Wilder et al. | |
| 5,115,126 A | 5/1992 | Ams et al. | |
| 5,353,786 A | 10/1994 | Wilk | |
| 5,488,696 A | 1/1996 | Brosnan | |
| 5,785,648 A | 7/1998 | Min | |
| 5,850,496 A | 12/1998 | Bellahsene et al. | |
| 6,616,603 B1 | 9/2003 | Fontana | |
| 6,880,945 B2 | 4/2005 | Knaack et al. | |
| 7,104,678 B2 | 9/2006 | De Lamberterie | |
| 7,150,714 B2 | 12/2006 | Myles | |
| 7,407,311 B2 | 8/2008 | Yang | |
| 7,460,751 B2 | 12/2008 | Gomez Ruiz | |
| 7,486,885 B2 * | 2/2009 | Tenmyo | G02B 6/0001 362/16 |
| 7,712,907 B2 * | 5/2010 | Zyka | G02B 5/045 362/16 |
| 7,874,982 B2 | 1/2011 | Selover | |
| 7,909,761 B2 | 3/2011 | Banchieri et al. | |
| 8,016,441 B2 * | 9/2011 | Birman | G01D 11/28 362/23.01 |
| 8,323,184 B2 | 12/2012 | Spiegal et al. | |
| 8,684,577 B2 | 4/2014 | Vayser | |
| 8,740,780 B2 * | 6/2014 | Honda | G02B 23/2469 362/574 |
| 9,615,884 B2 | 4/2017 | Armour et al. | |
| 2008/0064931 A1 | 3/2008 | Schena et al. | |
| 2010/0315816 A1 * | 12/2010 | Madelin | G03B 15/06 362/294 |
| 2011/0021877 A1 | 1/2011 | Fortier et al. | |
| 2012/0022333 A1 | 1/2012 | Main et al. | |
| 2012/0116362 A1 | 5/2012 | Kieturakis | |
| 2012/0130186 A1 | 5/2012 | Stopek et al. | |
| 2014/0379054 A1 * | 12/2014 | Cooper | A61F 9/0079 607/90 |
| 2016/0151639 A1 * | 6/2016 | Scharf | A61N 5/0601 607/92 |

OTHER PUBLICATIONS

U.S. Appl. No. 62/083,811, filed Nov. 24, 2014.
U.S. Appl. No. 13/625,357, filed Sep. 24, 2012, now U.S. Pat. No. 9,151,462.
U.S. Appl. No. 61/578,428, filed Dec. 21, 2011.

* cited by examiner

LIGHT DELIVERY SYSTEMS AND RELATED METHODS OF USE

CROSS REFERENCE TO RELATED APPLICATIONS

This application claims the benefit of U.S. Provisional App. No. 62/083,811 filed Nov. 24, 2014, all of which is herein incorporated by reference in its entirety; and claims priority to and is a continuation-in-part of co-pending U.S. patent application Ser. No. 13/625,357 filed Sep. 24, 2012, which claims priority to Provisional App. Ser. No. 61/578,428 filed Dec. 21, 2011, the entire contents of each are also hereby incorporated by reference in their entireties.

FIELD OF THE DISCLOSURE

The present disclosure relates to light delivery assemblies/systems and, more particularly to light delivery assemblies/systems that provide light to and/or illuminate/treat predetermined locations (e.g., surgical sites/targets), and related methods of use.

BACKGROUND OF THE DISCLOSURE

In general, providing good/sufficient light to a site/target (e.g., surgical site) can be problematic. Not only can overhead lights be unwieldy, they can be both a source of glare and of shadows simultaneously, making it difficult to see the surgical site and the video monitors. Head lamps also cast shadows, for example, of a surgeon's hands or instruments, and are intrinsically heavy (or require cumbersome connections to external light or power sources).

Small lamps and other light-emitting structures can be unnecessarily costly and complicated. They typically require bulbs or fiber-optical elements, as well as a source of power which potentially becomes an electric shock risk to the patient. Not only do they have multiple connections and bulky fixtures that complicate surgery, they can be problematic sources of heat. Also, a light fixture that incorporates elements such as light bulbs into a complex structure requires significant manufacturing costs.

Moreover, light sources (whether overhead or localized) can cause glares and reflections that are blinding or distracting. For example, light that glares off of monitors interferes with the ability of medical staff to monitor a patient's vital signs, and light reflecting from steel or mirrored surfaces and instruments can interfere with a surgeon's focus.

Furthermore, it is noted that the application of UV light or other sterilizing/disinfecting radiation can be helpful for medical and non-medical applications (e.g., where there is a risk of re-introduction of microbes and other kinds of contaminants).

Thus, an interest exists for improved light delivery assemblies/systems, and related methods of use. Moreover, an interest exists for improved light delivery assemblies/systems configured for the delivery of the full range of light spectra (e.g., UV light) for a range of applications (e.g., sterilization, disinfection, therapy, etc.). These and other inefficiencies and opportunities for improvement are addressed and/or overcome by the assemblies, systems and methods of the present disclosure.

SUMMARY OF THE DISCLOSURE

The present disclosure provides advantageous light delivery assemblies/systems, and improved methods for using the same. More particularly, the present disclosure provides improved light delivery assemblies/systems that provide light to and/or illuminate/treat predetermined locations (e.g., surgical sites/targets).

In exemplary embodiments, the present disclosure provides for a light delivery assembly that connects to an existing light source and illuminates/treats a pre-determined site/location (e.g., surgical site/target) from multiple directions (e.g., without causing glares and reflections). In some embodiments, the light delivery assembly includes an optional window/lens member and/or an optional cover member.

The assembly can be structured so that, when placed near a site with portions of the assembly extending around opposite sides of the site, light from the source is reflected within the assembly and emitted onto the site. Moreover, the outer shell of the assembly can provide a substantially opaque shield that prevents the light from causing glares and reflections in the surrounding environment.

In certain embodiments, the window member provides an inner shell that diffuses light to improve the quality of the light (e.g., for a surgeon), and/or encloses portions of the assembly to prevent contamination (e.g., to keep fluids out of the light).

In certain embodiments, assemblies of the present disclosure can be manufactured inexpensively, for example, from molded plastic. Thus, assemblies and methods are provided that can be used to provide improved light to a site (e.g., surgical site/target), allowing a user (surgeon) to perform a task (surgery) in good view without interference from shadows, structures, glares, heat, and other problems. Moreover, assemblies and methods are provided for the delivery of the full range of light spectra for a range of applications (e.g., illumination, therapy, sterilization, disinfection, etc.).

In certain embodiments, assemblies of the present disclosure include a shell with an open C-shaped cross-sectional profile with the open portion of the C facing inwards and downwards. The shell includes a substantially opaque material with an inner reflective surface. Light is received within the shell through an adaptor that couples to a light source (e.g., fiber optic light line). The light is both passed through a small slit in a reflector and reflected within the assembly using a faceted reflector (e.g., multi-faceted reflector), the inner reflective surface, or both and onto the site/target, while the over-hanging upper portion of the shell shades the user's eyes and the surrounding environment.

In certain aspects, the present disclosure provides a light delivery assembly that includes a connection feature to connect to a light source and receive light into the assembly, and a shell configured to at least partially surround a site (surgical incision) and diffuse the light inwards and downwards. The connection feature may be a fiber optic cable adapter where light is received into the assembly. The site is illuminated/treated substantially evenly from all sides while the shell shades items outside of and above the assembly from the light. The shell may have a cross-sectional shape describable as an inward-facing asymmetrical C-like shape. The shell may be shaped such that an upper surface of the shell overhangs a lower surface of the shell. A faceted (e.g., multi-faceted) reflector can be disposed within the assembly to reflect the light from the source through the assembly. In certain embodiments, the reflector has a shape like a truncated pyramid and presents four facets angled away from one another. A slit may be provided through the reflector to allow some light to pass directly to the site/surgical area.

The shell may have an overall shape that allows portions of it to be disposed on distal sides of a site. For example, in various embodiments, looking down on the shell shows it having a shape approximating a U, O, D, L, V, C, H, Y, or J or a square, diamond, oval, ellipse, rectangle, or other polygonal shape. In certain embodiments, an overall shape of the shell is circular or substantially circular (e.g., oblong or irregular). The shape of the shell also allows an instrument (e.g., surgical instrument) to be applied at various angles to the incision/site.

In certain aspects, the present disclosure provides a method for illuminating and/or treating a site of a medical procedure or the like. The method includes receiving light into a shell surrounding a site of a medical procedure and diffusing, by means of the shell, the light inwards and downwards towards the site substantially evenly from all sides while shading items outside of and above the assembly from the light. In some embodiments, diffusing the light includes reflecting the light from a reflective surface disposed around a majority of an inside surface of the shell. Light can be received into the shell from any suitable source (such as a fiber optic cable or other sources) and reflected off of one or more internal reflectors. Other sources of light include, without limitation, ultraviolet (UV) light sources, UVC light sources, light-emitting diodes (LEDs), Xenon, Br—Kr, Mercury, visible light, IR light, other wavelengths of light, etc.

In certain aspects, the present disclosure provides a light delivery assembly having a shell/housing with a cross-sectional shape similar to an inward-facing asymmetrical C, wherein the shell/housing is shaped to be placed proximal to a site and emit light onto the site from a plurality of directions while inhibiting the light from radiating away from the outside of the shell/housing. In some embodiments, the shell/housing is spaced away from the site in all directions when in use.

In some embodiments, the C-shaped structure forms a circle on itself and is open in the middle. Assemblies of the present disclosure can be fabricated from plastic or other suitable materials. Materials can be used that are rigid, non-translucent, or both. The non-translucent nature of portions of the assembly prevents light from reflecting in any direction that would interfere with visual acuity.

In some embodiments, the assembly includes a transparent or translucent window member that effectively encloses the light ring by covering the C-shaped portion of the light ring. The window member separates the reflective surface of the light ring from fluids (e.g., body fluids of the patient/user) by providing a physical barrier. In other aspects, the window member can modify light intensity and/or wavelength to achieve a preferred pattern of light distribution.

In certain embodiments, the upper surface of the assembly is wider and overhangs the lower surface to prevent light from interfering with visual acuity and to focus the light in an inferior and center direction onto the procedure site. The shell has an asymmetrical C-shaped cross-sectional profile, with the shell having an upper portion and a lower portion with the upper portion extending over the lower portion and extending further inwards than the lower portion to define the asymmetrical C-shaped cross-sectional profile of the shell.

The inner surface may be covered with a reflective coating, and angled in a manner that further allows light to be focused in a central and inferior direction. Light can enter the assembly via a cable (e.g., fiber optic cable) in certain embodiments. The cable can be connected to a variable output light source. In some embodiments, both the cable and the light source are separate from, and can be coupled to, and uncoupled from, the assembly. The fiber optic cable can be held in place by the cable adaptor. The adaptor can accommodate the cable, and also be long enough to cover the metal parts of the cable thus eliminating contact between metal parts of the cable and patient.

In certain embodiments, once light enters the assembly it encounters the light reflector. The reflector can be pyramidal in shape and covered with a reflective coating. This shape allows for reflectivity around the metalized inner surface of the shell/assembly. The reflector can include a slit in the middle to allow some passage of light directly into the inner circle. The slit may be large enough to allow for light to pass through, thereby eliminating shadows at the point of entry, but small enough to allow ample light to be reflected around the remainder of the assembly.

The assembly can be manufactured to different diameters to allow for different applications (e.g., surgical applications, disinfection/sterilization especially UV in the UVC wavelength range, other UV treatment, infrared heating and treatment, therapy, IR light delivery, use of all/other wavelengths of light, etc.). An adhesive strip can be applied to the assembly (e.g., during the manufacturing process), and the assembly incorporated into a surgical drape. The assembly can undergo gamma radiation sterilization as well as ethylene oxide sterilization and thus be used in sterile or non-sterile applications.

The present disclosure provides for a light delivery assembly including a shell having an asymmetrical C-shaped cross-sectional profile, the shell having an upper portion and a lower portion with the upper portion extending over the lower portion and extending further inwards than the lower portion to define the asymmetrical C-shaped cross-sectional profile of the shell; a light source to deliver light into the shell; wherein the shell is configured to at least partially surround a pre-determined location and diffuse the light inwards and downwards, via the asymmetrical C-shaped shell, toward the pre-determined location.

The present disclosure also provides for a light delivery assembly wherein the light source is configured to generate and deliver light selected from the group consisting of ultraviolet light, UVC light, xenon generated light, Br—Kr generated light, mercury generated light, visible light, IR light, halogen generated light, incandescent light, illuminating light, sterilizing light, therapeutic light, heating light, photo-luminescent light, phototherapeutic light, disinfecting light, fiber optic light, pulsed light and continuous light.

The present disclosure also provides for a light delivery assembly wherein the light source is an external light source and is mounted with respect to the shell via one or more cables or fibers. The present disclosure also provides for a light delivery assembly wherein the light source includes one or more light emitting diodes.

The present disclosure also provides for a light delivery assembly wherein the light source includes an external light source having one or more light emitting diodes, the external light source mounted with respect to the shell via one or more cables or fibers.

The present disclosure also provides for a light delivery assembly wherein the shell includes a connection feature to connect to the light source; and wherein one or more light emitting diodes are mounted with respect to the connection feature, the one or more light emitting diodes of the connection feature configured to deliver light into the shell and to the pre-determined location.

The present disclosure also provides for a light delivery assembly wherein the shell includes an inner surface; and wherein one or more light emitting diodes are mounted with respect to the inner surface, the one or more light emitting diodes of the inner surface configured to deliver light into the shell and to the pre-determined location.

The present disclosure also provides for a light delivery assembly wherein the shell defines an opening and includes a cover member configured and dimensioned to releasably mount with respect to the upper portion of the shell to cover the opening. The present disclosure also provides for a light delivery assembly wherein the cover member is configured and dimensioned to: (i) prevent light or radiation to escape from the upper portion of the shell, and (ii) direct light towards the pre-determined location.

The present disclosure also provides for a light delivery assembly wherein one or more light emitting diodes are mounted with respect to a lower surface of the cover member, the one or more light emitting diodes configured to deliver light into the shell or to the pre-determined location. The present disclosure also provides for a light delivery assembly wherein one or more reflectors are mounted with respect to a lower surface of the cover member, the one or more reflectors configured to direct light toward the pre-determined location.

The present disclosure also provides for a light delivery assembly wherein one or more optic fibers are mounted with respect to the cover member, each optic fiber in communication with an optical sensor; and wherein the optical sensor is configured to detect areas of the pre-determined location that have been treated with dye material so that a specific frequency, intensity or duration of light can be delivered to areas treated with dye material via the one or more optic fibers. The present disclosure also provides for a light delivery assembly wherein the one or more optic fibers each include flat end portions that are mounted with respect to a lower surface of the cover member.

The present disclosure also provides for a light delivery assembly wherein the wherein one or more optic fibers are mounted with respect to the shell, each optic fiber in communication with an optical sensor; and wherein the optical sensor is configured to detect areas of the pre-determined location that have been treated with dye material so that a specific frequency, intensity or duration of light can be delivered to areas treated with dye material via the one or more optic fibers.

The present disclosure also provides for a light delivery assembly wherein a window member is mounted with respect to the upper and lower portions of the shell, the window member configured to provide a barrier between the shell and the pre-determined location while permitting light from the shell to pass through the window member and to the pre-determined location. The present disclosure also provides for a light delivery assembly wherein the window member is configured and dimensioned to: (i) diffuse the light from the shell to improve the quality of the light delivered to the pre-determined location, and (ii) enclose at least a portion of the shell to prevent contamination of the shell.

The present disclosure also provides for a light delivery assembly wherein the shell includes a first shell member and a second shell member, the first and second shell members configured to mount with respect to one another to define the shell; and wherein the first and second shell members are adjustable and movable relative to one another so that a user can change the size of the shell.

The present disclosure also provides for a light delivery assembly wherein the shell is configured and dimensioned to be positioned in-line with a breathing/ventilator circuit so that as gases pass through the center of the shell, the gases are exposed to the light that is directed inwards via the shell.

The present disclosure also provides for a light delivery assembly including a shell having an asymmetrical C-shaped cross-sectional profile, the shell defining an opening and having an upper portion and a lower portion with the upper portion extending over the lower portion and extending further inwards than the lower portion to define the asymmetrical C-shaped cross-sectional profile of the shell; a cover member configured and dimensioned to releasably mount with respect to the upper portion of the shell to cover the opening; a light source to deliver light into the shell; wherein the shell is configured to at least partially surround a pre-determined location and diffuse the light inwards and downwards, via the asymmetrical C-shaped shell, toward the pre-determined location; wherein the cover member is configured and dimensioned to: (i) prevent light or radiation to escape from the upper portion of the shell, and (ii) direct light towards the pre-determined location; wherein one or more light emitting diodes are mounted with respect to a lower surface of the cover member, the one or more light emitting diodes configured to deliver light into the shell or to the pre-determined location; wherein one or more reflectors are mounted with respect to the lower surface of the cover member, the one or more reflectors configured to direct light toward the pre-determined location; and wherein a window member is mounted with respect to the upper and lower portions of the shell, the window member configured to provide a barrier between the shell and the pre-determined location while permitting light from the shell to pass through the window member and to the pre-determined location.

The present disclosure also provides for a method for delivering light including providing a shell having an asymmetrical C-shaped cross-sectional profile, the shell having an upper portion and a lower portion with the upper portion extending over the lower portion and extending further inwards than the lower portion to define the asymmetrical C-shaped cross-sectional profile of the shell; at least partially surrounding a pre-determined location with the shell; providing light into the shell via a light source; delivering and diffusing the provided light inwards and downwards, via the asymmetrical C-shaped shell, toward the pre-determined location.

Any combination or permutation of embodiments is envisioned. Additional advantageous features, functions and applications of the disclosed systems, methods and assemblies of the present disclosure will be apparent from the description which follows, particularly when read in conjunction with the appended figures. All references listed in this disclosure are hereby incorporated by reference in their entireties.

BRIEF DESCRIPTION OF THE DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various steps, features and combinations of steps/features described below and illustrated in the figures can be arranged and organized differently to result in embodiments which are still within the scope of the present disclosure. To assist those of ordinary skill in the art in making and using the disclosed assemblies, systems and methods, reference is made to the appended figures, wherein.

DETAILED DESCRIPTION OF DISCLOSURE

Figure 1A:
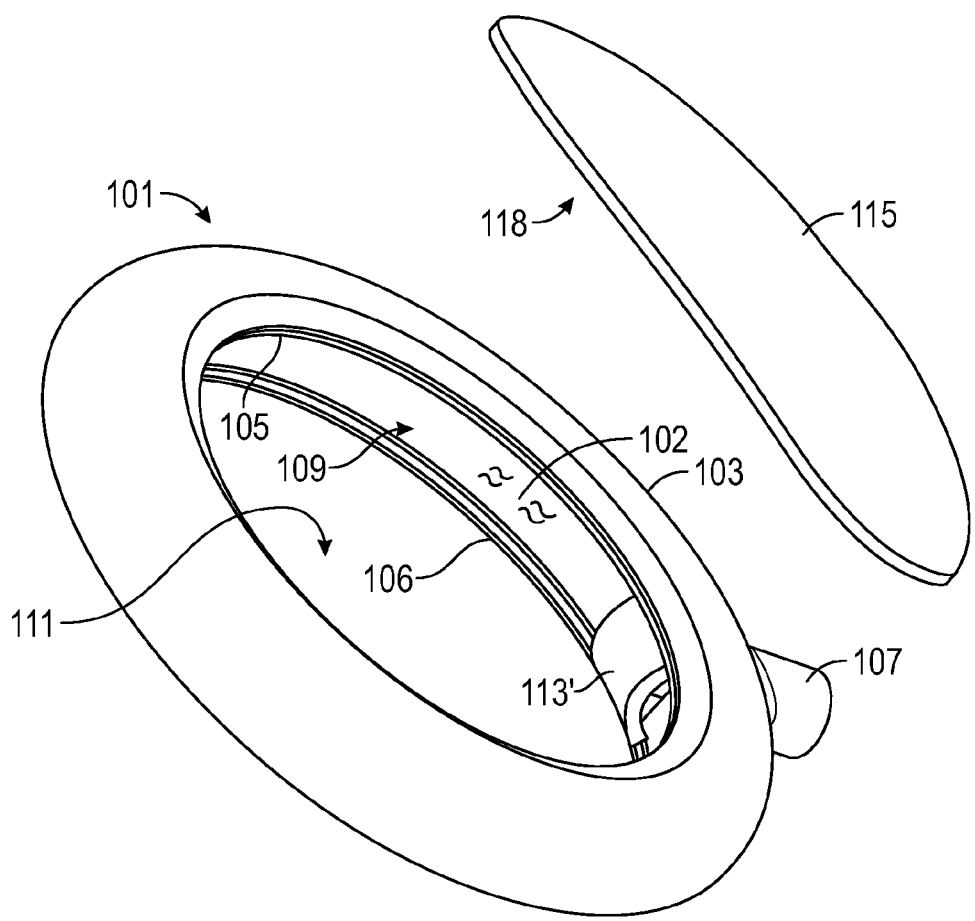
FIGS. 1A-1E show an exemplary light delivery assembly of the present disclosure.

The exemplary embodiments disclosed herein are illustrative of advantageous light delivery assemblies, and systems of the present disclosure and methods/techniques thereof. It should be understood, however, that the disclosed embodiments are merely exemplary of the present disclosure, which may be embodied in various forms. Therefore, details disclosed herein with reference to exemplary light delivery assemblies/fabrication methods and associated processes/techniques of assembly and use are not to be interpreted as limiting, but merely as the basis for teaching one skilled in the art how to make and use the advantageous light delivery assemblies/systems and/or alternative assemblies of the present disclosure.

The present disclosure provides improved light delivery assemblies/systems, and associated methods for using the same. More particularly, the present disclosure provides advantageous light delivery assemblies/systems that provide light to and/or illuminate/treat predetermined locations (e.g., surgical sites).

The present disclosure provides methods and assemblies for illuminating and/or treating a site (e.g., surgical site). Assemblies and methods of the present disclosure can be used with surgical instruments in surgical procedures requiring illumination/treatment.

Examples of surgical procedures that may employ assemblies and methods of the present disclosure include, without limitation, laparoscopic and endoscopic procedures, insertion of anchors and fixation devices, including rods, plates and cables, trochars, injection ports, or procedures benefiting from improved illumination/treatment (e.g., illumination, UV disinfection/sterilization especially UV in the UVC wavelength range, other UV treatment, infrared heating and treatment, therapy, IR light delivery, use of all/other wavelengths of light, etc.).

Referring now to the drawings, like parts are marked throughout the specification and drawings with the same reference numerals, respectively. Drawing figures are not necessarily to scale and in certain views, parts may have been exaggerated for purposes of clarity.

With reference to FIGS. 1A-1E, there is illustrated an embodiment of an exemplary light delivery assembly 101 according to the present disclosure. In general, light delivery assembly 101 is configured and dimensioned to provide light to and/or illuminate/treat predetermined locations (e.g., surgical sites).

In general and as further discussed below, assembly 101 can be utilized for medical applications on people's bodies and within people's bodies (e.g., illumination, UV disinfection/sterilization especially UV in the UVC wavelength range, other UV treatment, infrared heating and treatment, therapy, IR light delivery, use of all/other wavelengths of light, etc.). Moreover, it is noted that there are also similar uses of assembly 101 (and the other assemblies discussed below) on inanimate objects in medical facilities, in laboratories of various kinds, in industry and elsewhere. For example, use of the assembly 101/shell 103 to apply UV or other sterilizing/disinfecting radiation is particularly valuable for these medical and non-medical applications where there is a risk of re-introduction of microbes and other kinds of contaminants. In general, assembly 101 (and the other assemblies discussed below) can be utilized for the delivery of the full range of light spectra for a range of applications (e.g., illumination, therapy, sterilization, disinfection, etc.).

FIG. 1A gives a perspective view of assembly 101 showing shell 103 and connection feature/coupling 107. Reflector 113' (or 113) can be mounted substantially within shell 103. Shell 103, as shown in FIG. 1A, forms a ring (light ring) having a cross-sectional shape substantially like an asymmetrical C with an upper portion 105 overhanging a lower portion 106. Stated another way, exemplary shell 103 has an asymmetrical C-shaped cross-sectional profile, with the shell 103 having an upper portion 105 and a lower portion 106 with the upper portion 105 extending over the lower portion 106 and extending further inwards than the lower portion 106 to define the asymmetrical C-shaped cross-sectional profile of the shell 103.

Shell 103 can also include inner reflective surface 109.

Figure 1B:
Figure 1C:
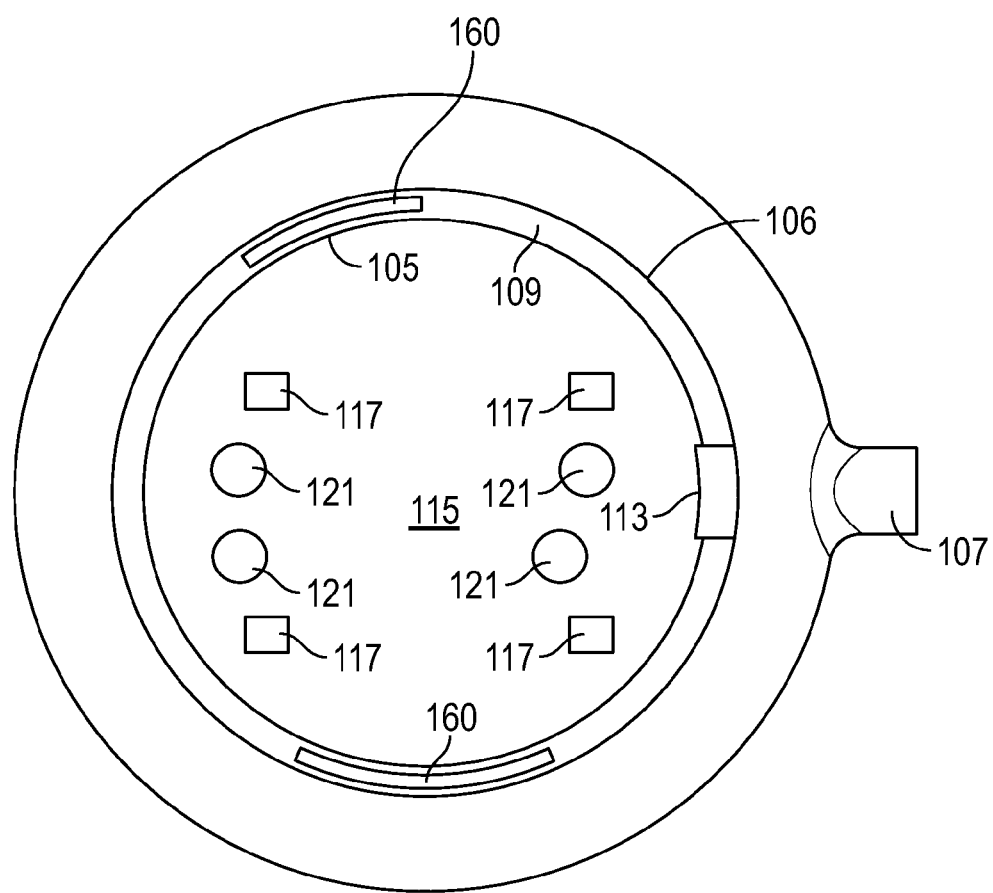

FIG. 1B shows a side view of assembly 101. FIG. 1C shows a bottom view, showing a portion of reflector 113 and overhang (upper portion) 105 presenting inner surface 109 in a downward (inferior) direction.

Figure 1D:
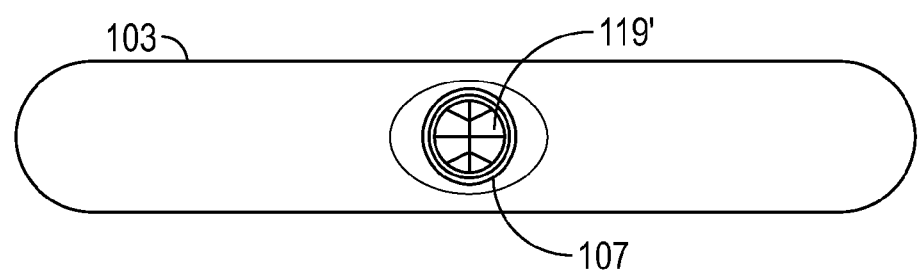
Figure 1E:
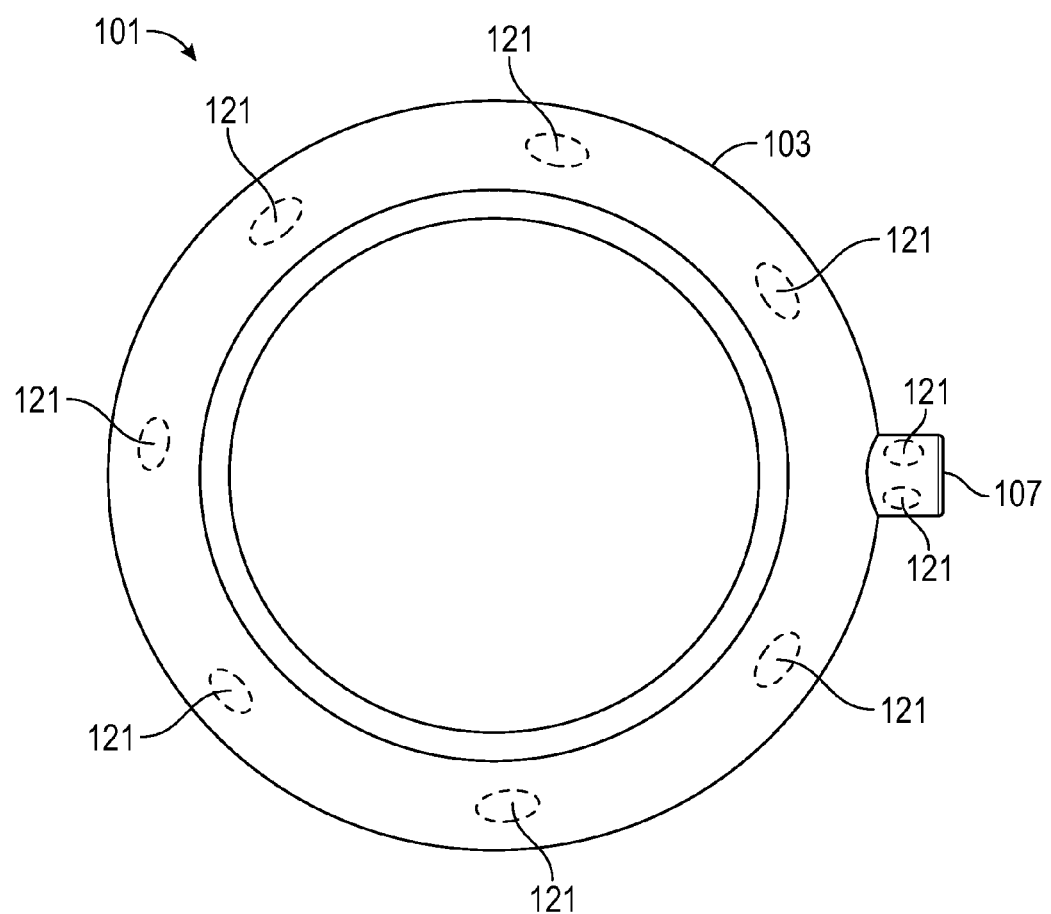

FIG. 1D shows a front view through connection feature 107, revealing faceted surface 119' of reflector 113'. FIG. 1E gives a top view of assembly 101.

FIGS. 2A-2D show exemplary reflector 113 according to certain embodiments. As can be seen, for example, in FIG. 2A, reflector 113 includes faceted surface (e.g., multi-faceted surface) 119 that is angled towards incoming light arriving through connection feature 107. Due to the fact that exemplary faceted surface 119 presents a plurality of surfaces angled away from one another, incoming light is reflected in a plurality of directions into shell 103. Within shell 103, the light is reflected and re-reflected throughout the shell 103 while also being reflected out of the shell 103 in an inward and downward direction (e.g., towards the pre-determined location or site).

While FIG. 1A, for example, shows shell 103 being substantially circular in overall shape, it is appreciated that other shapes are possible and can also be adapted to reflect light inwardly and downwardly. For example, a closed curve or polygonal shape can perform as described, as will shapes with a plurality of arms radiating away from reflector 113, such as a V shape or U shape with reflector 113 and connection feature 107 at a point such as the base of the U or V, along one of the arms, or at one or both of the tips of the U or the V.

In certain embodiments and as shown in FIG. 1A, assembly 101 can include an optional window/lens member 102 (e.g., transparent or translucent window member 102) positioned between the light ring of shell 103 and the site to be illuminated/treated. In general, the window member 102 provides a physical barrier (to fluids/gases, etc.) between the reflective surface 109 of the shell 103 and the site/patient, and protects the reflective surface 109 from contamination (while letting light to pass through window 102). In certain aspects, the window member 102 can modify light intensity and/or wavelength to achieve a preferred pattern of light distribution. In some embodiments and as shown in FIG. 1A, window member 102 can extend from upper portion 105 to lower portion 106 and around/above the inner surface 109 to prevent fluids/gases and the like from contacting inner surface 109, while letting light (e.g., UV light) from inner surface 109/shell 103 to pass through window 102 and to the site.

In some embodiments, the window member 102 provides an inner shell/barrier that diffuses light to improve the quality of the light (e.g., for a surgeon), and/or encloses portions of the assembly 101 to prevent contamination (e.g., to keep fluids out of the light ring/inner surface 109). As such, the assembly 101 can include a transparent or translucent window member 102 that effectively encloses the light ring by covering the C-shaped portion of the light ring. The window member 102 separates the reflective surface 109 of the light ring/shell 103 from fluids (e.g., body fluids of the patient/user) by providing a physical barrier. In other aspects, the window member 102 can modify light intensity and/or wavelength to achieve a preferred pattern of light distribution.

Figure 2A:
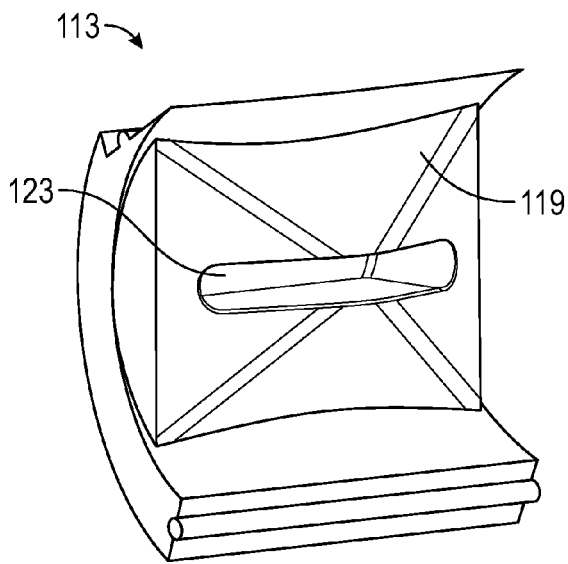
FIGS. 2A-2D show an exemplary multi-faceted reflector according to certain embodiments.
Figure 2B:
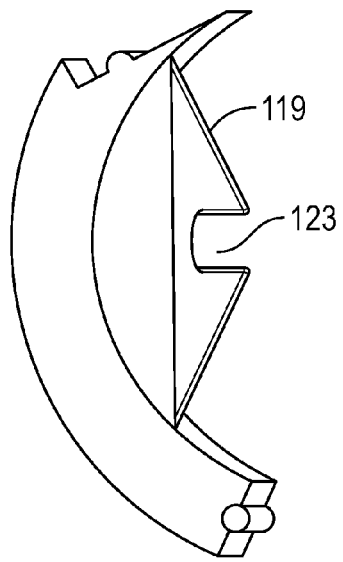

FIG. 2B shows structural features that can be included at the top and bottom of reflector 113 allowing it to be snapped into place, or fitted into (mounted with respect to), shell 103. In other embodiments, reflector 113 is integral with at least a portion of shell 103.

Figure 2C:
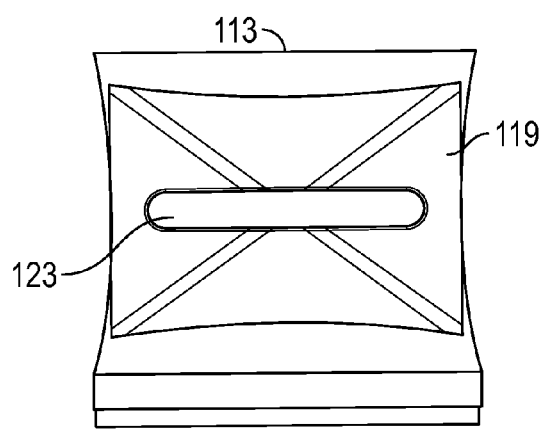

FIG. 2C illustrates that slit 123 extends completely through reflector 113. Slit 123 can be provided to allow light to pass directly from the light source to the site. The aperture area of slit 123 can be varied by design (e.g., from zero to a few cm²) to modulate a ratio of an amount of light penetrating directly through slit 123 to the site to an amount of light reflected via internal surface 109 of shell 103 to the site. Different users/surgeons or different applications may benefit from one ratio or another according to preferences or circumstances.

Figure 2D:
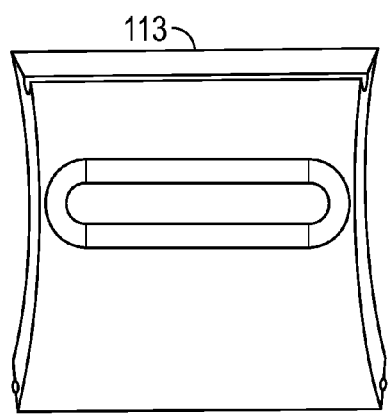

FIG. 2D shows the aperture in the back of the housing of reflector 113 for slit 123.

Figure 3:
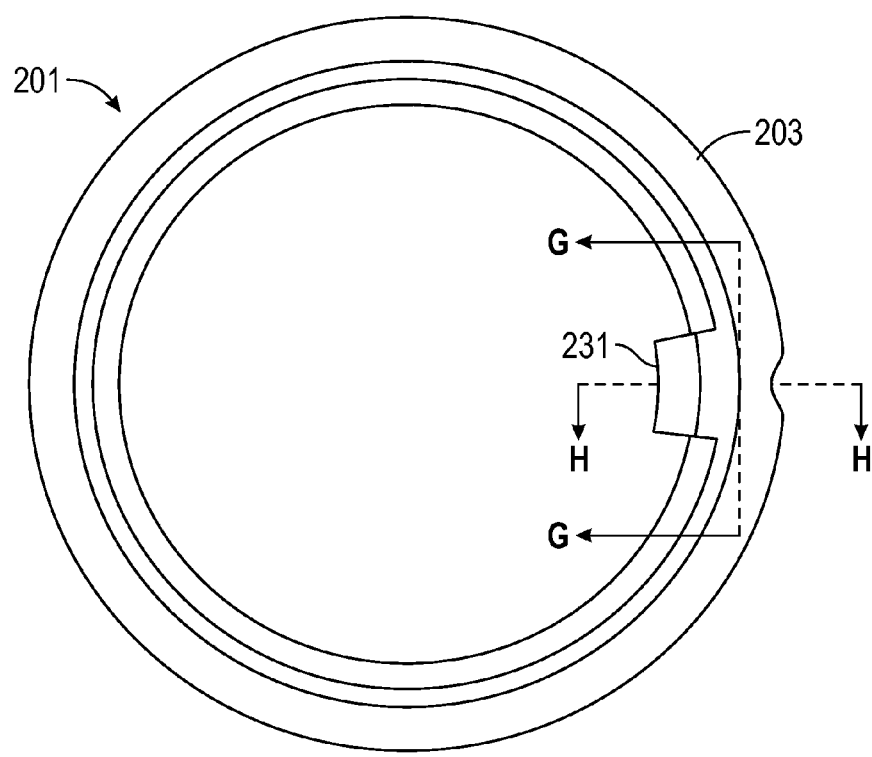
FIG. 3 shows another light delivery assembly according to certain embodiments.

FIG. 3 shows a light delivery assembly 201 according to alternative embodiments. Assembly 201 as shown in FIGS. 3-6 is constructed from an upper shell 203, and a base or lower shell 204. This morphology may be easy and inexpensive to mold. As shown in FIG. 3, exemplary upper shell 203 includes extension boss 231 to house reflector 113.

Figure 4:
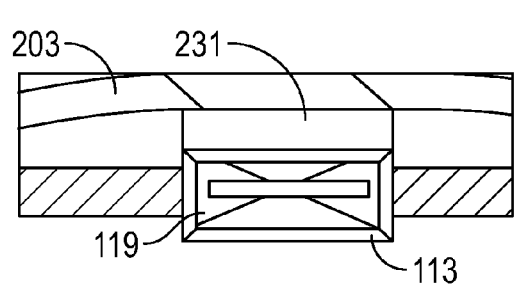
FIG. 4 shows a section of the assembly of FIG. 3.

FIG. 4 shows a section of device 201 taken along line G shown in FIG. 3. As can be seen in FIG. 4, boss 231 holds reflector 113 in place (e.g., according to the geometry shown in FIGS. 9 and 10) so that facets 119 are exposed through coupling 207. It is noted that coupling 207 can be mounted with respect to upper shell 203 (FIG. 6B), or to lower shell 204 (FIG. 6A).

Figure 5:
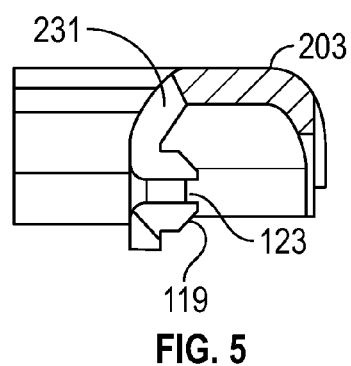
FIG. 5 shows another section of the assembly of FIG. 3.

FIG. 5 shows a section of assembly 201 along line H shown in FIG. 3. As illustrated here, the arrangement of boss 231 and reflector 113 positions slit 123 to allow light to pass through and illuminate a site (e.g., via shells 203, 204 and slit 123).

Figure 6A:
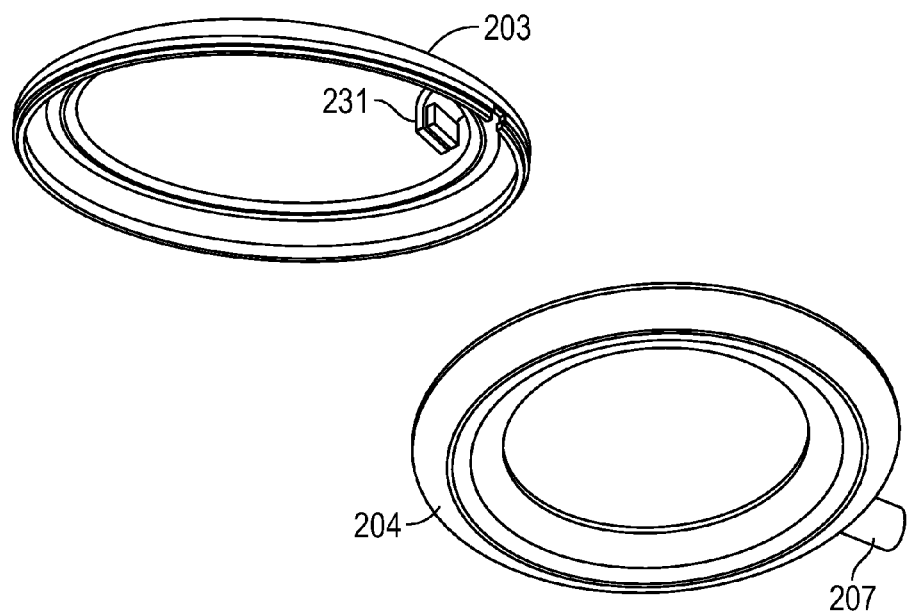
FIGS. 6A and 6B show components of a light delivery assembly according to certain embodiments.

FIG. 6A gives a perspective view of upper shell 203 and a base shell 204 of assembly 201 according to certain embodiments. Not only does manufacturing assembly 201 according to a two-component design provide an easy to mold and lightweight snap-together assembly, by positioning connection feature/coupling 207 and boss 231 on opposed components, the arrangement for assembling the shapes is made visually evident. This allows a user-assembled assembly 201 to be provided, for example, as two separate components (203, 204). In some embodiments, upper shell 203 and base shell 204 are packaged and shipped one nested within the other, or as stacks of each separately nested, for compact packaging and shipping. Boss 231 can be integral with upper shell 203 (or lower shell 204), and can then snap or mount with respect to lower shell 204 (or upper shell 203) during assembly.

Figure 6B:
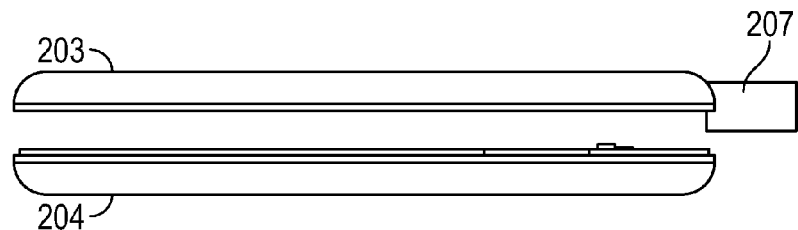

FIG. 6B illustrates assembly of upper shell 203 and base shell 204. Upper shell 203 and a base shell 204 can each be fabricated separately, of a suitable material (e.g., plastic). An inside surface of upper shell 203, base shell 204, or both can be coated with a reflective material. Components of assemblies of the present disclosure can be formed of any suitable surgical material such as, for example, plastic, surgical stainless steel, resin, glass, foil, fiberboard, other materials known in the art, or combinations thereof. Further suitable materials may include epoxy, titanium or other metals, ceramics, composites, rubbers, or polymers.

Referring back to FIG. 1A, reflective surface 109 on the inside of shell 103 can be provided by any suitable means. In some embodiments, reflective surface 109 includes a coating of a reflective material, such as a metallic material. In some embodiments, surface 109 includes foil disposed within shell 103. Surface 109 may include a mirror, for example, a glass, crystal, or plastic mirror, that is curved and disposed within shell 103.

Figure 7:
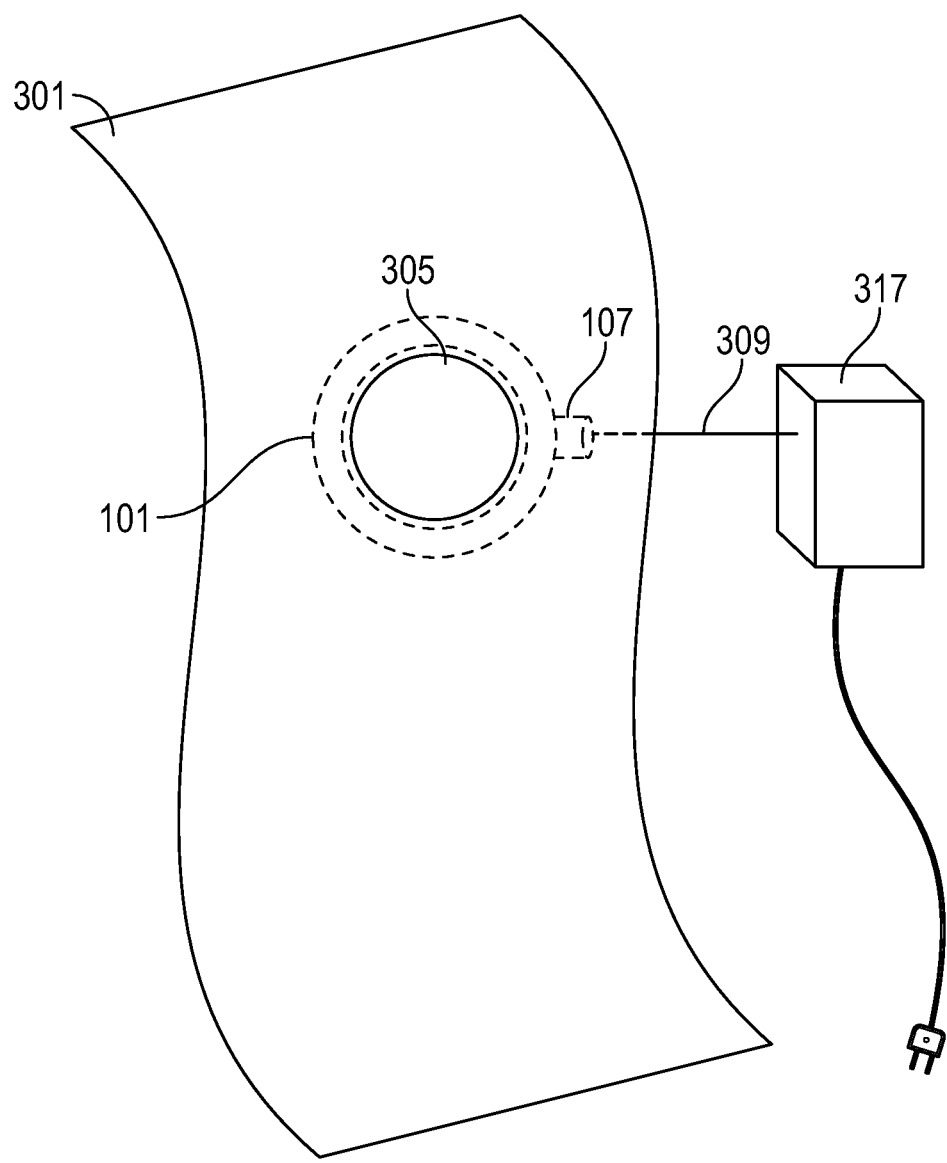
FIG. 7 illustrates use of an exemplary light delivery assembly according to certain embodiments.

FIG. 7 illustrates use of exemplary assembly 101 according to certain embodiments. Sterile surgical sheet 301 may be placed over a site for an incision. Sheet 301 may have hole 305 for surgery. Assembly 101 may be located under sheet 301 and connected to light source 317 via cable (e.g., fiber optic cable) 309.

Assembly 101 includes connection feature 107 which can include an adaptor to couple to cable 309 (e.g., fiber optic cable or fiber optic light line) from light source 317. The light source 317 may include glass fiber optic cables, plastic fiber optic cables or any other suitable means for transmitting and emitting light. Light source 317 may be any suitable device for producing light such as, for example, a halogen or incandescent light box or other light source 317 readily available in hospital settings. Suitable light sources 317 are available from Welch Allyn Inc. (Skaneateles Falls, N.Y.). The light source 317 may have any suitable power level. Other types of light sources 317 include, without limitation, ultraviolet (UV) light sources, UVC light sources, light-emitting diodes (LEDs), Xenon, Br-KR, Mercury, visible light, IR light sources, other wavelengths of light, etc.

In certain embodiments, light source 317 is the XLS-300 High-Powered 300 W xenon light source from Olympus Corporation (Shinjuku, Tokyo, JP). Any other suitable light source 317 capable of producing light that is transmitted via the light transmitters, such as fiber optic cables, may also be used. Light sources and optic cables are discussed in U.S. Pat. No. 5,850,496 and U.S. Pat. No. 5,115,126, and surgical illumination generally is discussed in U.S. Pat. No. 5,785, 648; U.S. Pat. No. 6,616,603; U.S. Pat. No. 7,150,714; and U.S. Pat. No. 5,353,786, the contents of each of which are incorporated by reference in their entireties.

It is noted that light source 317 (e.g., light box) can include one or more LEDs that generate the light (e.g., visible or UV or UVC or other wavelengths of light) for assembly 101 (or 201). As such, LEDs associated with source 317 and external to assembly 101 can generate the light, with the light being provided to assembly 101 via cable(s) 309 (e.g., via fiber optic tube(s) or cable(s)).

Moreover, it is noted that in addition to or in lieu of light being provided to assembly 101 via light source 317 (via external light source 317), light (e.g., visible or UV or UVC or other wavelengths of light) can be provided to assembly 101 (to shell 103) via one or more LEDs 121 positioned/mounted with respect to coupling 107, as shown in FIG. 1E. For example, the interior of coupling 107 can include one or more LEDs 121 that provide light for assembly 101 (FIG. 1E). It is noted that coupling 107 can include and/or be associated with any suitable number of LEDs 121.

Furthermore, it is noted that in addition to or in lieu of light being provided to assembly 101 via light source 317 and/or via LEDs of coupling 107, light can be provided to assembly 101 (to shell 103) via one or more LEDs 121 positioned/mounted with respect to coupling shell (e.g., to inner surface 109), as shown in FIG. 1E. For example, the inner surface 109 of shell 103 can include one or more LEDs 121 distributed/mounted thereon that provide light for assembly 101 (FIG. 1E). It is noted that shell 103/inner surface 109 can include and/or be associated with any suitable number of LEDs 121.

Providing assembly 101 with circular or other open-format morphology of shell 103 allows a user/surgeon to work freely in the area surrounded by assembly 101. In some embodiments, an outer diameter of assembly 101 is between about 2 inches and about 10 inches. In certain embodiments, an outer diameter of assembly 101 is between 4 and 8 inches, or about 5 to about 7 inches. Moreover, assembly 101 can be spaced away from the incision or from surgical instruments. Surgical light is discussed in U.S. Pat. No. 7,909,761; U.S. Pat. No. 5,488,696; and U.S. Pat. No. 4,605,990, the contents of each of which are incorporated by reference in their entirety.

In some embodiments, assembly 101 is provided with an adhesive, such as a peel-and-stick adhesive on one surface. Removing the peel-off backing allows sheet 301 to be fixed into place on assembly 101. In certain embodiments, assembly 101 is provided with a sheet 301 attached, for example, with an adhesive.

While reflector 113 is discussed herein having a pyramidal aspect, other embodiments are within the scope of the present disclosure. In some embodiments, reflector 113 has two facets 119. Facets 119 of reflector 113 may be flat, curved, or irregular. Reflector 113 can include any suitable number of facets 119.

Figure 8A:
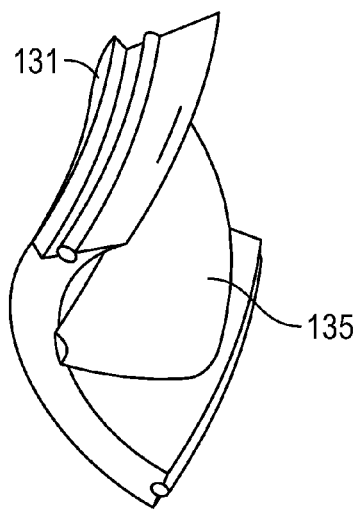
FIGS. 8A-8D show an exemplary reflector according to certain embodiments.
Figure 8B:
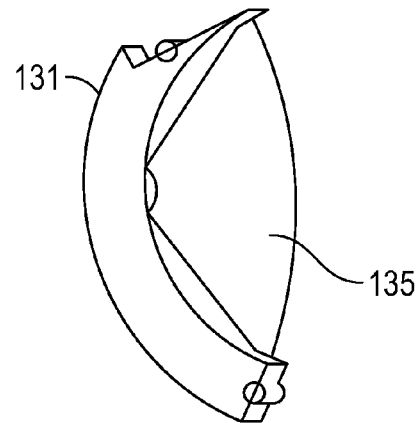
Figure 8C:
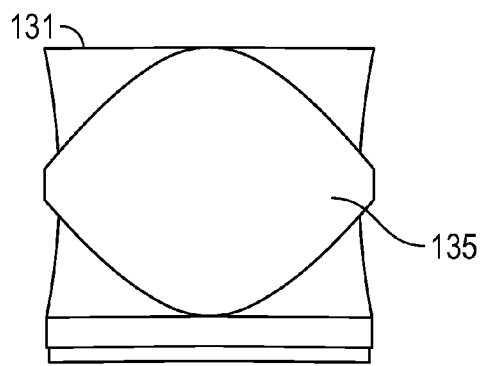

FIG. 8A gives a perspective view of another reflector 131 according to certain embodiments. As can be seen, for example, in side view in FIG. 8B or front view in FIG. 8C, reflector 131 may have a substantially convex curved face 135 and operate to provide some benefits of the present disclosure.

Figure 8D:
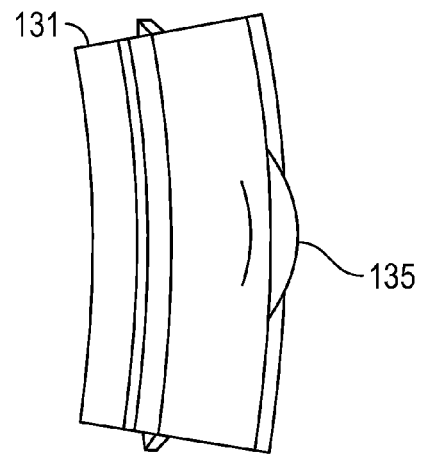

FIG. 8D shows a top view of reflector 131, illustrating the outer housing, which may be plastic, and face 135. This assemblage can be assembled into assembly 101. Preferably, reflector 113, reflector 131, or the like is assembled into assembly 101 opposed to connection feature 107 according to a geometry that reflects light throughout the assembly (and to a site).

Figure 9A:
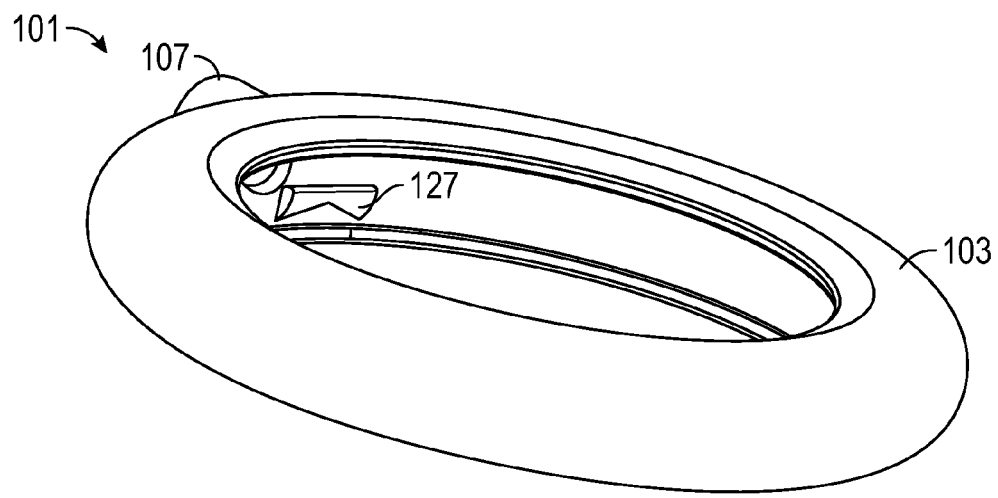
FIGS. 9A-9B illustrate an of arrangement of components in an assembly of the present disclosure.
Figure 9B:
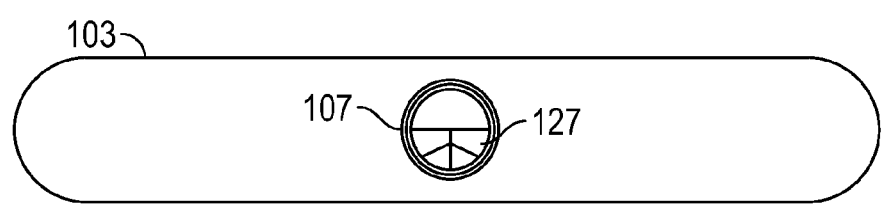

FIGS. 9A-9B illustrate a geometry of arrangement of components within assembly 101. Reflector 127, which may have the illustrated morphology or any other morphology described herein or useful for illumination, is opposed to connection feature 107.

Figure 10A:
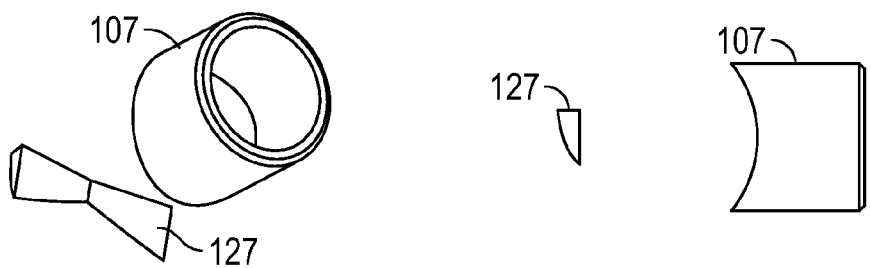
FIGS. 10A-10B give a detailed view of an arrangement of exemplary components.
Figure 10B:
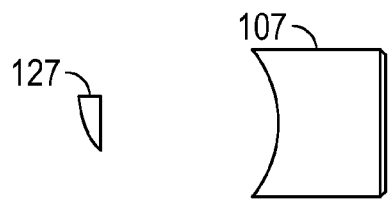

FIG. 10A-10B show a spatial relationship between reflector 127 and connection feature 107. In some embodiments, connection feature 107 has a substantially cylindrical portion defining an axis. The axis of feature/coupling 107 may extend into a surface of the reflector 127. However, in certain embodiments, for example where slit 123 is present, the axis of feature 107 does not intersect the reflector (113) but rather passes by or through it (e.g., through slit 123).

Assemblies and methods of the present disclosure provide significant advantages over prior systems for providing illumination during a procedure (e.g., surgical procedure). The assembly minimizes the requirement of cumbersome cables, headlights, overhead fixtures, and power sources, while allowing direction of light to an ideal location. Assembly 101 does not compromise or reduce the working area, as it is spaced away from the incision/site, and provides superior illumination of the procedure site without inducing glare or affecting the user's/surgeon's visual acuity. Assemblies and methods of the present disclosure help people see a field (surgical field) when overhead operating room lights need to be dimmed or turned off. The site is illuminated without creating a glare on the monitor screen or in a person's eyes, creating a more efficient and safer environment for users/surgeons, operating room staff and patients.

Assemblies and methods of the present disclosure improve efficiency or flow of surgical procedures by avoiding the need to repeatedly adjust overhead lights and thereby eliminate the need for the people's eyes to accommodate to different lighting conditions; they increase the visibility of ports while changing instruments; eliminate the questionable practice of removing camera or light from inside a patient's abdomen or pelvis to illuminate a surgical site; enhance visualization of the surgical field when preparing and inserting mesh and other implants; improve visualization of sharps on the surgical field reducing the risk of accidental punctures to staff; reduce the risk of injury to surgical assistants and OR staff by improving the ability to monitor robotic arm movement during surgery; allow for estimation of blood loss around surgical ports; allow staff to maintain correct count of surgical instruments, sponges and sharps on the field; and can be employed as a teaching device allowing students to see location of such ports/trochars/devices without turning on overhead lights.

Figure 11:
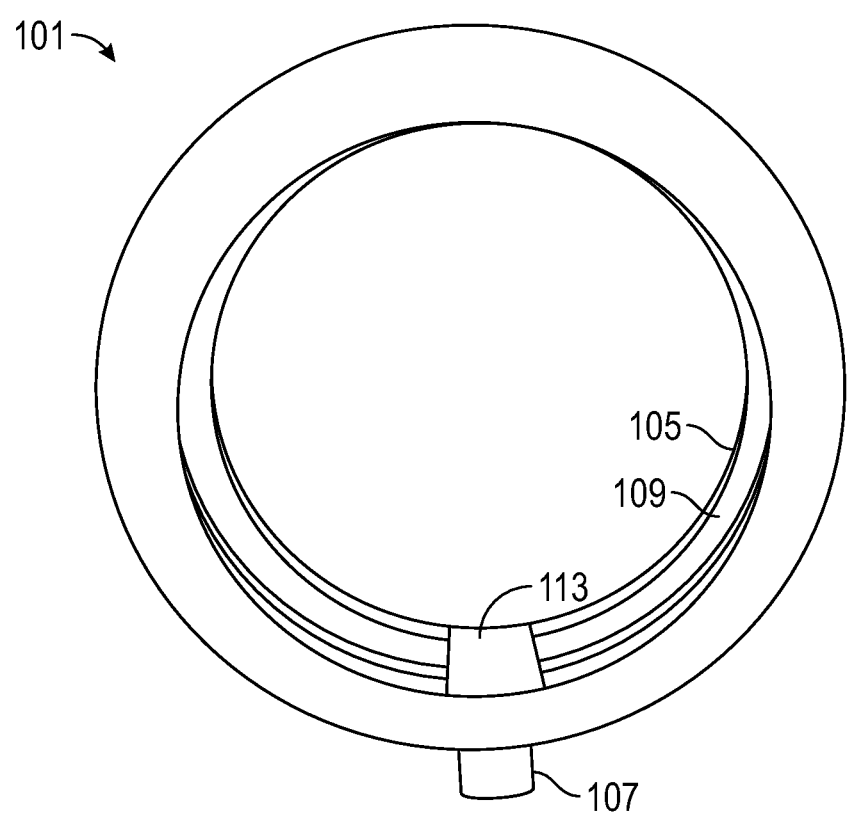
FIG. 11 is an image of a fabricated device according to exemplary embodiments of the present disclosure.

FIG. 11 is an image of an exemplary assembly 101 that was fabricated. Assemblies and methods of the present disclosure are inexpensive to manufacture, and work in conjunction with existing operating room equipment and technology.

Assemblies and methods of the present disclosure can be used for purposes including but not limited to: illumination; visualization using dyes or the like for both diagnostic and therapeutic purposes; sterilization of a procedural field; delivery of therapeutic light for the treatment of disorders of various tissues and organs (e.g., skin, membranes, connective tissue, hair, skeletal, neurological, renal, cardiovascular, eye, endothelium, blood and bone marrow); heating; photoluminescence; phototherapies; and assessment of organ function including blood flow. Additional applications include invasive radiology, various imaging modalities and enhancing teaching techniques. Assemblies of the present disclosure can be sterilized by suitable means.

In general, in addition to utilizing assembly 101 for the medical applications on people's bodies and within people's bodies (e.g., illumination, UV disinfection/sterilization especially UV in the UVC wavelength range, other UV treatment, infrared heating and treatment, use of other wavelengths of light, etc.), it is again noted that there are also similar uses on inanimate objects in medical facilities, in laboratories of various kinds, in industry and elsewhere. For example, use of the assembly 101/shell 103 to apply UV or other sterilizing/disinfecting radiation is particularly valuable for these medical and non-medical applications where there is a risk of re-introduction of microbes and other kinds of contaminants.

Referring back to FIGS. 1A and 1C, assembly 101 can include optional cover member 115. In general, cover member 115 is configured and dimensioned to releasably mount with respect to shell 103 (e.g., to upper portion 105 of shell 103) and cover/close the aperture/opening 111 defined by shell 103.

In exemplary embodiments, cover member 115 has at least two primary purposes: (1) to prevent escape of radiation from the assembly 101 thus protecting user's/medical personnel and others in the vicinity, and (2) to direct light (which could be of any wavelength) onto the desired target/site.

In one embodiment, cover member 115 is fabricated from a flat opaque material that prevents escape of radiation from the assembly 101, thus protecting medical personnel and others in the vicinity.

Moreover and as shown in FIG. 1C, cover member 115 can include one or more reflectors 117. In general, reflectors 117 are mounted with respect to the lower surface 118 of cover member 115. In exemplary embodiments, each reflector 117 is configured and dimensioned to direct light from the assembly 101 (e.g., from shell 103) onto the patient or other surface to achieve a substantially uniform light distribution or any other light distribution that may be desired. It is noted that in addition to or in lieu of reflectors 117, lower surface 118 can include a reflective material/surface or the like, as similarly noted with inner surface 109 (e.g., includes a coating of a reflective material, and/or include mirrors or the like).

Furthermore and also as shown in FIG. 1C, cover member 115 can include one or more LEDs 121. In general, LEDs 121 are mounted with respect to the lower surface 118 of cover member 115. It is noted that cover member 115 can include any combination or permutation of reflectors 117 and/or LEDs 121 (e.g., only reflectors 117, only LEDs 121, both reflectors 117 and LEDs 121, no reflectors 117 and no LEDs 121, etc.). In exemplary embodiments, each LED 121 is configured and dimensioned to generate light (in any wavelength) and direct the light onto the patient or other surface to achieve a substantially uniform light distribution in a given wavelength or any other light distribution that may be desired.

In exemplary embodiments, it is noted that the surface to be treated with UV or other light (via assembly 101 or via the other assemblies of the present disclosure) may be painted/treated with dyes so that sensors or the like can be used to adjust the radiation delivered depending on where the dyes are applied and what types of dyes are applied in a given location.

Dyes can also be used as part of photodynamic therapy. Such dyes create free radicals when exposed to various wavelengths of light. These free radicals in turn kill pathogens.

Figure 12A:
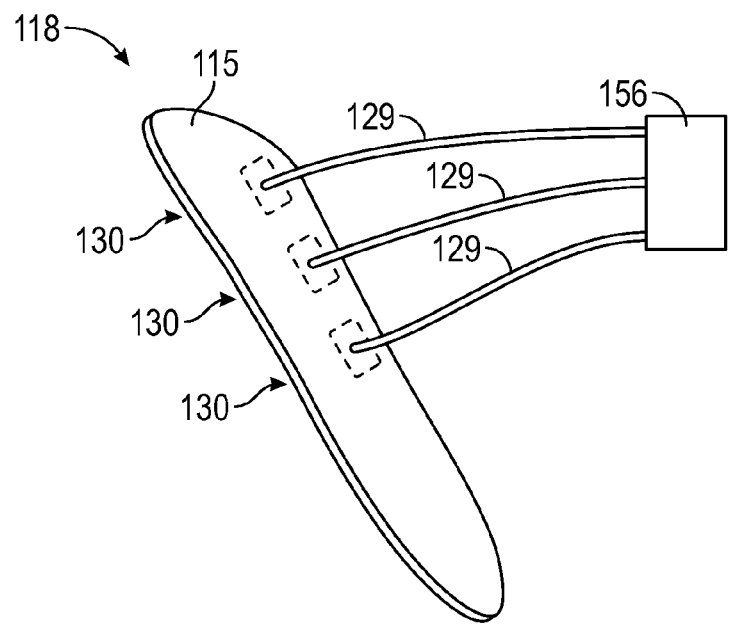
FIG. 12A shows another exemplary cover member of the present disclosure.

As shown in FIG. 12A, one exemplary way of detecting the areas that have been painted/treated with dyes and of delivering the radiation is to arrange/position one or more fiber optic fibers 129 such that the proximal ends of the fibers 129 includes a flat surface 130. In exemplary embodiments, the flat surface 130 is mounted with respect to cover member 115 (e.g., to lower surface 118 of cover member 115), although the present disclosure is not limited thereto. In some embodiments, flat surfaces 130 are positioned/mounted in the plane of cover member 115 (e.g., in the plane of lower surface 118). In other embodiments, the flat surfaces 130 are positioned in a plane substantially parallel to cover member 115, but closer to the site/surface having the dye (e.g., in a plane closer to the site to be treated).

In certain embodiments, there is either: 1) an optical sensor 156 at the distal end of each of the fiber optic fibers 129, or 2) one or more optical sensors 156 which sequentially optically connect with the distal end of each of the optical fibers 129.

Depending on whether dye has been applied and what color of dye has been applied at a location on the surface near the proximal end of each of the fiber optic fibers 129 (as detected by sensor 156), a specific frequency, intensity and/or duration of light will be delivered to that surface area by that optic fiber 129 (as determined by sensor 156). This exemplary system can be used for sterilization/disinfection or other treatments of the surface, including medical treatment of the skin or other body parts of human or animal patients. Treatments may include ultraviolet light (either UVC or other wavelengths) or infrared light or other wavelengths of light.

As such, the present disclosure provides for systems for guiding (e.g., in vivo) light delivery (e.g., via sensor-based systems with feedback functionality, or via image-based guidance systems, and/or via programmed light delivery based on activation of selected fibers or light delivery channels).

Figure 12B:
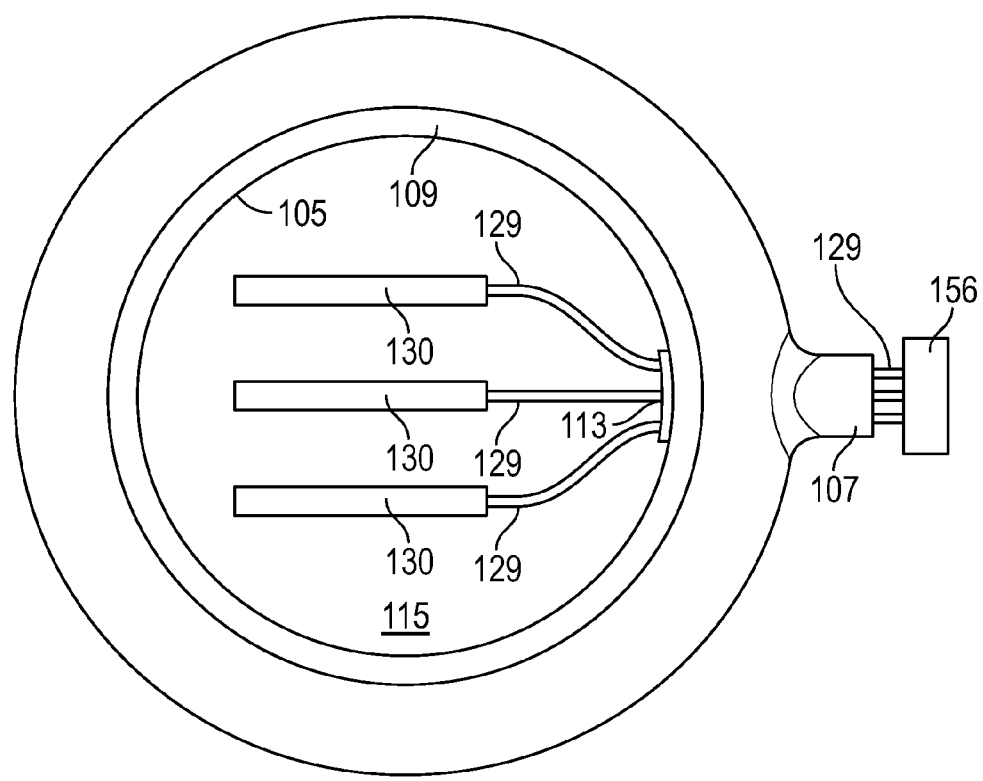
FIG. 12B shows another exemplary light delivery assembly and cover member of the present disclosure.

FIG. 12B depicts another embodiment of a cover member 115 having flat surfaces 130 mounted with respect to cover member 115 (e.g., to lower surface 118). Fibers/cables 129 connect flat surfaces 130 to one or more sensors 156 for therapy/treatment (e.g., dye-based photodynamic therapy), as similarly discussed above in connection with FIG. 12A.

Figure 12C:
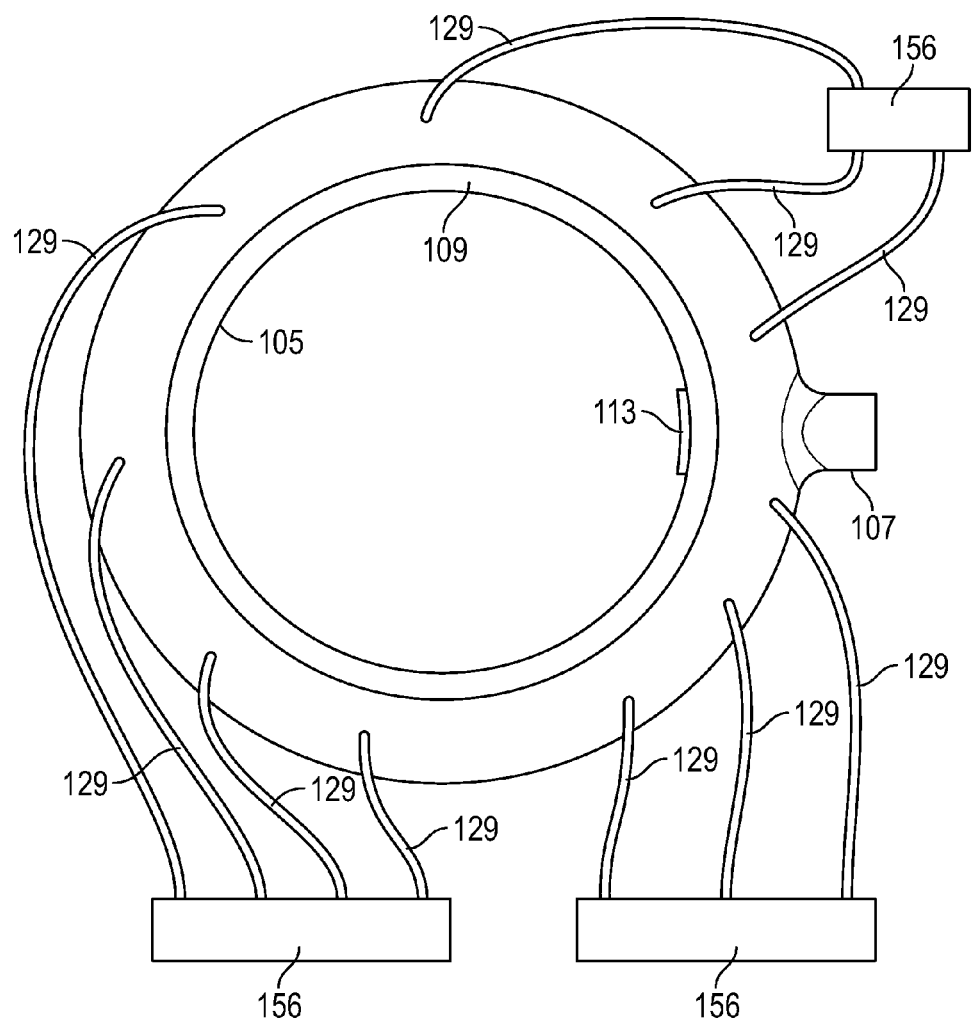
FIG. 12C shows another exemplary light delivery assembly of the present disclosure.

In another embodiment and as shown in FIG. 12C, shell 103 is associated with one or more fibers 129. Fibers 129 are in communication with one or more sensors 156 for therapy/treatment via fibers 129, as similarly discussed above. In exemplary embodiments, the proximal end of each fiber 129 is positioned along inner surface 109 (e.g., flush with inner surface 109) for treatment purposes (e.g., for dye-based photodynamic therapy—discussed above). As shown in FIG. 12C, the fibers 129 can be positioned/spaced along inner surface 109 in such a manner as to provide improved assessment and location of where the dyes have been applied (e.g., for treatment purposes).

In other embodiments, the present disclosure provides for an ultraviolet light (or other wavelength range or mixture of wavelengths) delivery system/assembly 101 in an open ring shaped configuration (e.g., to reduce or eliminate contamination of gases in a breathing/ventilator circuit or the like). The light is capable of inactivating bacteria, viruses and fungi or other pathogens. The light may be delivered either continuously or in a pulsed mode.

In one embodiment, the shell 103 (e.g., inner surface 109) is lined with a reflective material capable of reflecting and/or refracting light so the radiation is directed toward the lumen 111 of the shell 103. Light enters the shell 103 from a cable 309 (e.g., fiber optic cable) and is dispersed by a reflecting/refracting lens 102 or lenses 102. In such embodiments, it is noted that assembly 101 may or may not include reflector 113 or the like.

The shell 103 can be positioned in-line with the breathing/ventilator circuit or the like (e.g., to reduce or eliminate contamination of gases in the breathing/ventilator circuit or the like). As gases pass through the center of the shell 103 they are exposed to the radiation being directed toward the center of the shell 103. The light is capable of inactivating bacteria, viruses and fungi or other pathogens, and the light may be delivered either continuously or in a pulsed mode.

In other embodiments, the shell 103 is covered on the inside with LEDs 121 (FIG. 1E) that generate ultraviolet light (or other wavelength range or mixture of wavelengths) and direct the light toward the lumen 111 of the shell/ring 103. The shell 103 can be positioned in-line with the breathing/ventilator circuit or the like. As gases pass through the center of the shell 103 they are exposed to the radiation being directed toward the center of the shell 103.

In some embodiments, the shell 103 contains or is associated with (e.g., on the inside surface 109) one or more rigid or flexible fiber optic tubes 160 (as described further below) that generate ultraviolet light (or other wavelength range or mixture of wavelengths) and direct the light toward the lumen 111 of the shell 103. In such embodiments, assembly 101 typically does not include cover member 115. The shell 103 can be positioned in-line with the breathing/ventilator circuit or the like. As gases pass through the center of the shell 103 they are exposed to the radiation being directed toward the center of the shell 103.

In addition to generating and delivering light by the assemblies/structures discussed above, it is noted that visible, UV or other wavelengths of light may be generated and delivered by a rigid or flexible fiber optic tube 160 that delivers light along its length either in all directions (e.g., like a tubular fluorescent light bulb), or in specific directions along its length.

In exemplary embodiments, tube 160 takes the form of a rigid or flexible tube capable of transmission of all wavelengths of light generated separately, or generated within the tube 160. Exemplary tube 160 can be inserted into a body cavity to deliver the various wavelengths of light. Also contained within the tube 160 can be a visible light pointer used for aiming the tube 160 at specific places on or within the body.

In certain embodiments, tube 160 is a cylindrical tube that can accept all wavelengths of light (e.g., UV, visible, IR, etc.) from an exogenous light source, or tube 160 has the capability of generating its own light frequencies and directs these frequencies toward the distal end of the cylinder 160 and projects it onto an object/site (e.g., internal organ, skin, appendage). To aim the light beam, a second, visible stream of light is emitted from the cylinder 160 in a relationship to the first light beam, which allows the first light beam to be aimed at an appropriate target/site.

In some embodiments (e.g., to reduce or eliminate contamination of gases in the breathing/ventilator circuit or the like), exemplary assembly includes window/lens member 102, and includes a second inlet (or outlet) that is positioned about 180 degrees opposite the coupling 107. This second inlet allows for air from the breathing/ventilator circuit to flow into the shell 103, get exposed to the light (e.g., UV light), and then exit 180 degrees from where it entered.

Figure 13:
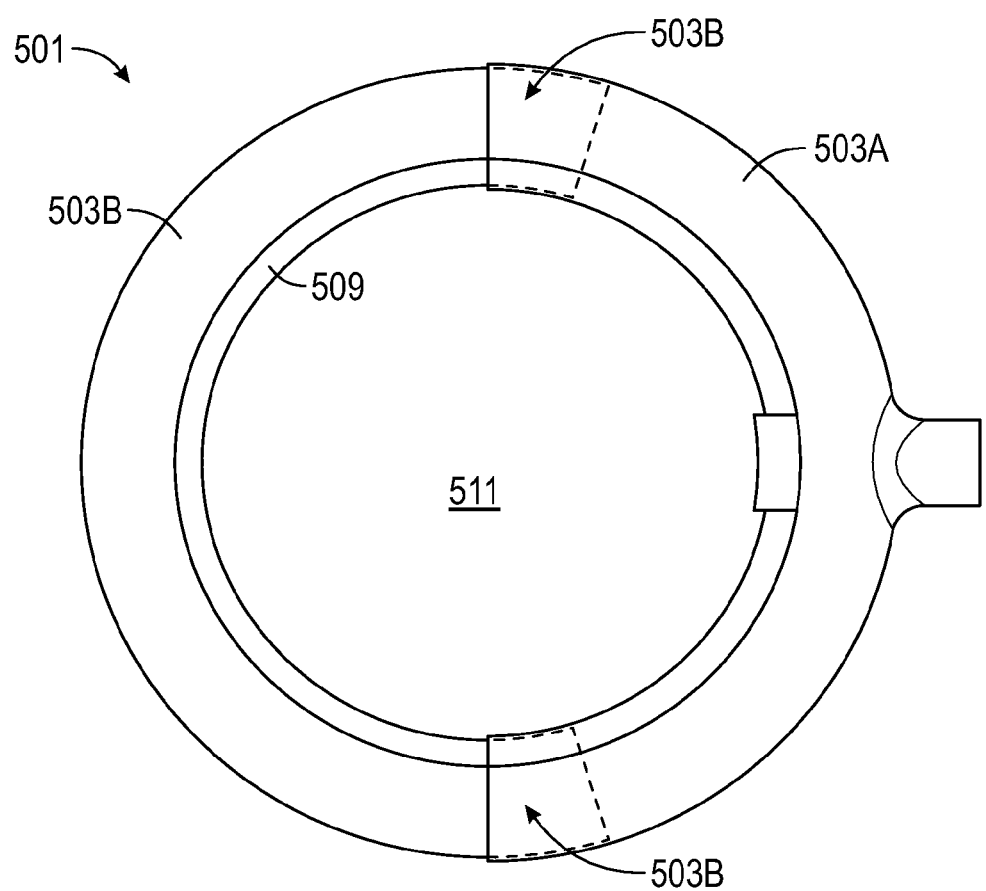
FIG. 13 shows another exemplary light delivery assembly the present disclosure.

In other embodiments and as shown in FIG. 13, exemplary light delivery assembly 501 is similar to assembly 101 discussed above, with some differences. Similar to assembly 101 discussed above, light delivery assembly 501 is configured and dimensioned to provide light to and/or illuminate/treat predetermined locations (e.g., surgical sites).

Exemplary assembly 501 includes shell member 503A and shell member 503B that are configured to mount with respect to one another to define opening 511, and to define inner surface 509 (e.g., a surface similar to surface 109).

In general, shell members 503A and 503B are adjustable/movable relative to one another so that a user can change the size of opening 511 defined by mounted shell members 503A, 503B. It is also noted that shell member 503B can be removed from shell member 503A, and shell member 503A can then be used without member 503B to provide light to and/or illuminate/treat predetermined locations (or vice versa).

In certain alternative embodiments, assemblies and methods of the present disclosure incorporate multiple structures (e.g., 101) to provide light both above and below the incision site. Dual-device structures are provided, for example, for use with single incision laparoscopic surgery procedures (SILS). Such procedures may employ an SILS port. See, e.g., U.S. Pub. 2012/0130186; U.S. Pub. 2012/0022333; U.S. Pub. 2011/0021877; and U.S. Pub. 2010/0249523, the contents of each of which are incorporated by reference in their entirety.

Two of assembly 101 that are permanently attached one on top of the other can form a multi-structure assembly/system according to an alternative embodiment. The light port lies at the junction of the two light rings and is anchored in place during the manufacturing process to the upper lip of the lower ring. This forms a seal that prevents the escape of gasses from the body cavity during the laparoscopic procedure. The shell 103 of each assembly 101 can be constructed from non-translucent material (e.g., plastic) and has a reflective inner surface 109.

In certain embodiments, the upper one of assembly 101 has two light adaptors. The first adaptor is in a longitudinal plane as above. The second light adaptor is oriented in a vertical plane and is used to provide light to the lower light ring. A direct connection between upper and lower assemblies 101 is aligned and forms a channel to allow light from the second adaptor to pass through the upper assembly 101 to the lower assembly 101. The light then encounters the light reflector, which will reflect light around the lower assembly 101. Light is then directed by the reflective surface in an inferior direction thereby illuminating the body cavity and the in vivo surgical site. An inflatable seal located on the outer diameter of the upper assembly 101 may be provided to prevent gasses from escaping the body cavity. Single-incision procedures are discussed in U.S. Pub. 2012/0116362 and U.S. Pub. 2008/0064931, the contents of which are incorporated by reference.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A light delivery assembly comprising:
    a shell having an asymmetrical C-shaped cross-sectional profile, the shell having an upper portion and a lower portion with the upper portion extending over the lower portion and extending further inwards than the lower portion to define the asymmetrical C-shaped cross-sectional profile of the shell, the C-shaped cross-sectional profile being asymmetrical about a plane including the boundary between the upper and lower portions;
    a light source to deliver light into the shell;
    wherein the shell is configured to at least partially surround a pre-determined location and diffuse the light inwards and downwards, via the asymmetrical C-shaped shell, toward the pre-determined location.

2. The assembly of claim 1, wherein the light source is configured to generate and deliver light selected from the group consisting of ultraviolet light, UVC light, xenon generated light, Br—Kr generated light, mercury generated light, visible light, IR light, halogen generated light, incandescent light, illuminating light, sterilizing light, therapeutic light, heating light, photo-luminescent light, phototherapeutic light, disinfecting light, fiber optic light, pulsed light and continuous light.

3. The assembly of claim 2, wherein the light source is an external light source and is mounted with respect to the shell via one or more cables or fibers.

4. The assembly of claim 1, wherein the light source includes one or more light emitting diodes.

5. The assembly of claim 1, wherein the light source includes an external light source having one or more light emitting diodes, the external light source mounted with respect to the shell via one or more cables or fibers.

6. The assembly of claim 1, wherein the shell includes a connection feature to connect to the light source; and
    wherein one or more light emitting diodes are mounted with respect to the connection feature, the one or more light emitting diodes of the connection feature configured to deliver light into the shell and to the pre-determined location.

7. The assembly of claim 1, wherein the shell includes an inner surface; and
    wherein one or more light emitting diodes are mounted with respect to the inner surface, the one or more light emitting diodes of the inner surface configured to deliver light into the shell and to the pre-determined location.

8. The assembly of claim 1, wherein the shell defines an opening and includes a cover member configured and dimensioned to releasably mount with respect to the upper portion of the shell to cover the opening.

9. The assembly of claim 8, wherein the cover member is configured and dimensioned to: (i) prevent light or radiation to escape from the upper portion of the shell, and (ii) direct light towards the pre-determined location.

10. The assembly of claim 8, wherein one or more light emitting diodes are mounted with respect to a lower surface of the cover member, the one or more light emitting diodes configured to deliver light into the shell or to the pre-determined location.

11. The assembly of claim 8, wherein one or more reflectors are mounted with respect to a lower surface of the cover member, the one or more reflectors configured to direct light toward the pre-determined location.

12. The assembly of claim 8, wherein one or more optic fibers are mounted with respect to the cover member, each optic fiber in communication with an optical sensor; and
    wherein the optical sensor is configured to detect areas of the pre-determined location that have been treated with dye material so that a specific frequency, intensity or duration of light can be delivered to areas treated with dye material via the one or more optic fibers.

13. The assembly of claim 12, wherein the one or more optic fibers each include flat end portions that are mounted with respect to a lower surface of the cover member.

14. The assembly of claim 1, wherein the wherein one or more optic fibers are mounted with respect to the shell, each optic fiber in communication with an optical sensor; and
    wherein the optical sensor is configured to detect areas of the pre-determined location that have been treated with dye material so that a specific frequency, intensity or duration of light can be delivered to areas treated with dye material via the one or more optic fibers.

15. The assembly of claim 1, wherein a window member is mounted with respect to the upper and lower portions of the shell, the window member configured to provide a bather between the shell and the pre-determined location while permitting light from the shell to pass through the window member and to the pre-determined location.

16. The assembly of claim 15, wherein the window member is configured and dimensioned to: (i) diffuse the light from the shell to improve the quality of the light delivered to the pre-determined location, and (ii) enclose at least a portion of the shell to prevent contamination of the shell.

17. The assembly of claim 1, wherein the shell includes a first shell member and a second shell member, the first and second shell members configured to mount with respect to one another to define the shell; and
    wherein the first and second shell members are adjustable and movable relative to one another so that a user can change the size of the shell.

18. The assembly of claim 1, wherein the shell is configured and dimensioned to be positioned in-line with a breathing/ventilator circuit so that as gases pass through the center of the shell, the gases are exposed to the light that is directed inwards via the shell.

19. A light delivery assembly comprising:
    a shell having an asymmetrical C-shaped cross-sectional profile, the shell defining an opening and having an upper portion and a lower portion with the upper portion extending over the lower portion and extending further inwards than the lower portion to define the asymmetrical C-shaped cross-sectional profile of the shell, the C-shaped cross-sectional profile being asymmetrical about a plane including the boundary between the upper and lower portions;
    a cover member configured and dimensioned to releasably mount with respect to the upper portion of the shell to cover the opening;
    a light source to deliver light into the shell;
    wherein the shell is configured to at least partially surround a pre-determined location and diffuse the light inwards and downwards, via the asymmetrical C-shaped shell, toward the pre-determined location;

wherein the cover member is configured and dimensioned to: (i) prevent light or radiation to escape from the upper portion of the shell, and (ii) direct light towards the pre-determined location;

wherein one or more light emitting diodes are mounted with respect to a lower surface of the cover member, the one or more light emitting diodes configured to deliver light into the shell or to the pre-determined location;

wherein one or more reflectors are mounted with respect to the lower surface of the cover member, the one or more reflectors configured to direct light toward the pre-determined location; and wherein a window member is mounted with respect to the upper and lower portions of the shell, the window member configured to provide a barrier between the shell and the pre-determined location while permitting light from the shell to pass through the window member and to the pre-determined location.

* * * * *